United States Patent
Falwell et al.

(10) Patent No.: US 7,331,958 B2
(45) Date of Patent: Feb. 19, 2008

(54) HANDLE DESIGN FOR A MEDICAL CATHETER

(75) Inventors: Gary S. Falwell, Moultonborough, NH (US); Charles A. Gibson, Malden, MA (US); Steven J. Burns, Haverhill, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 408 days.

(21) Appl. No.: 10/475,941

(22) PCT Filed: Apr. 26, 2002

(86) PCT No.: PCT/US02/13273

§ 371 (c)(1),
(2), (4) Date: May 10, 2004

(87) PCT Pub. No.: WO02/087455

PCT Pub. Date: Nov. 7, 2002

(65) Prior Publication Data

US 2004/0181140 A1    Sep. 16, 2004

Related U.S. Application Data

(60) Provisional application No. 60/287,057, filed on Apr. 27, 2001.

(51) Int. Cl.
*A61B 18/18* (2006.01)
*A61M 31/00* (2006.01)

(52) U.S. Cl. ................................. 606/41; 604/95.04

(58) Field of Classification Search ............. 604/95.01, 604/95.04; 606/41, 47–50
See application file for complete search history.

(56) References Cited

U.S. PATENT DOCUMENTS

| | | | | |
|---|---|---|---|---|
| 5,195,968 | A | * | 3/1993 | Lundquist et al. ....... 604/95.04 |
| 5,358,478 | A | * | 10/1994 | Thompson et al. ...... 604/95.04 |
| 5,383,852 | A | | 1/1995 | Stevens-Wright et al. |
| 5,462,527 | A | * | 10/1995 | Stevens-Wright et al. .. 604/528 |
| 5,611,777 | A | * | 3/1997 | Bowden et al. .......... 604/95.01 |
| 6,241,727 | B1 | * | 6/2001 | Tu et al. ....................... 606/41 |
| 6,315,778 | B1 | * | 11/2001 | Gambale et al. .............. 606/41 |
| 6,616,628 | B2 | * | 9/2003 | Hayzelden ............... 604/95.04 |

FOREIGN PATENT DOCUMENTS

EP      0 790 066 A     8/1997

* cited by examiner

*Primary Examiner*—Michael Peffley
(74) *Attorney, Agent, or Firm*—Wolf, Greenfield & Sacks, P.C.

(57) ABSTRACT

A handle for use with a catheter, the handle including a housing, a cable, and a guide. The housing has a proximal end, a distal end, and a longitudinal axis that extends from the proximal end of the housing to the distal end of the housing. The cable is disposed in the housing and extends through the proximal end of the housing. A portion of the cable that is disposed in the housing is movable, under compression, in a first direction that is substantially aligned with the longitudinal axis of the housing. The guide is disposed in the housing and is adapted to prevent the portion of the cable from moving in a second direction that is transverse to the first direction when the portion of the cable is moved in the first direction. The handle is suitable for use with an electrophysiology catheter having an elongated shaft.

65 Claims, 8 Drawing Sheets

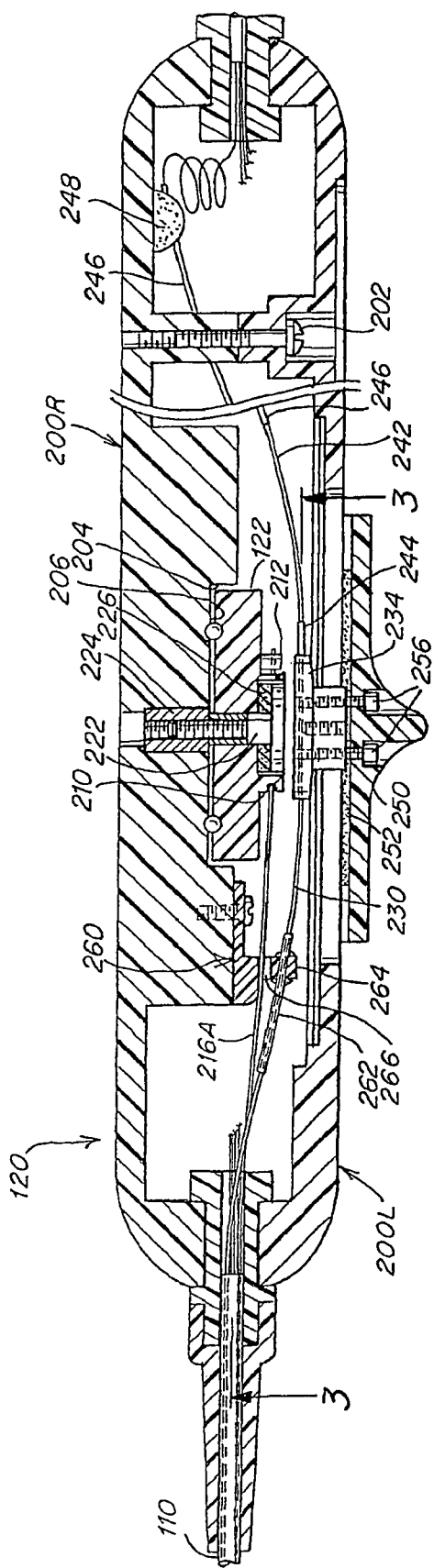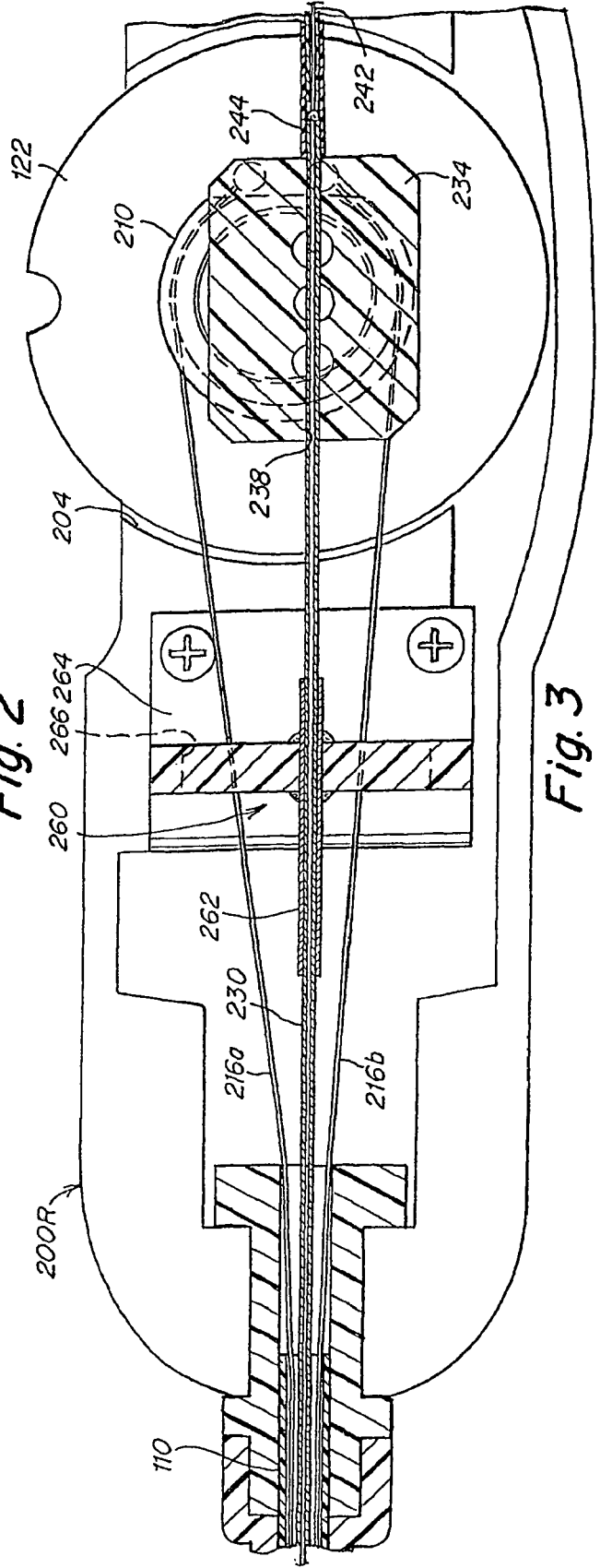

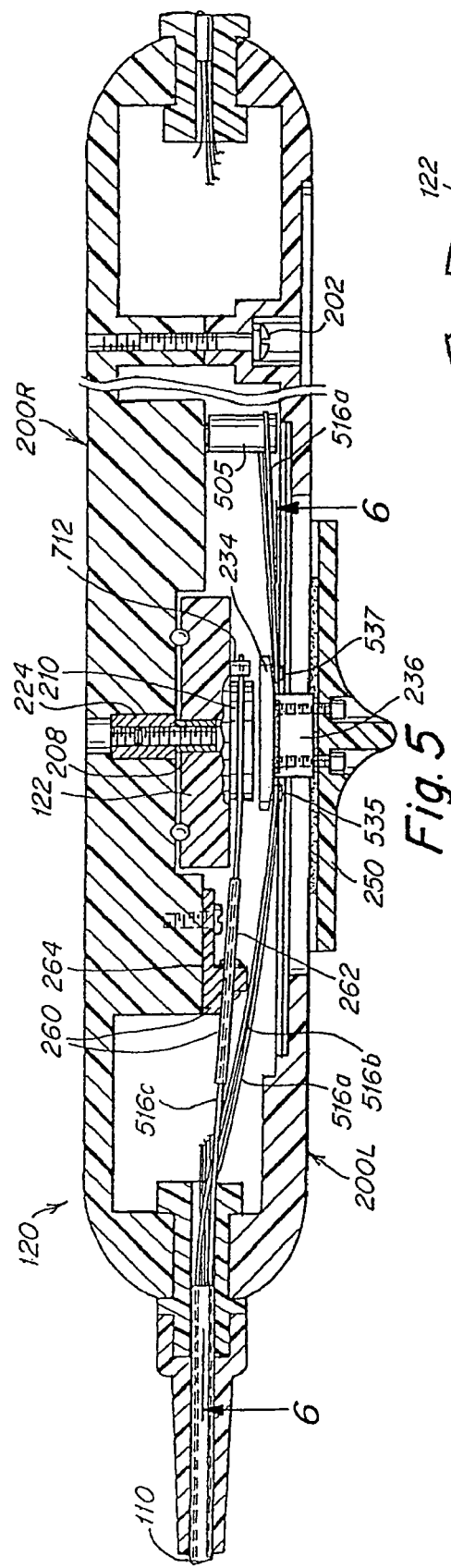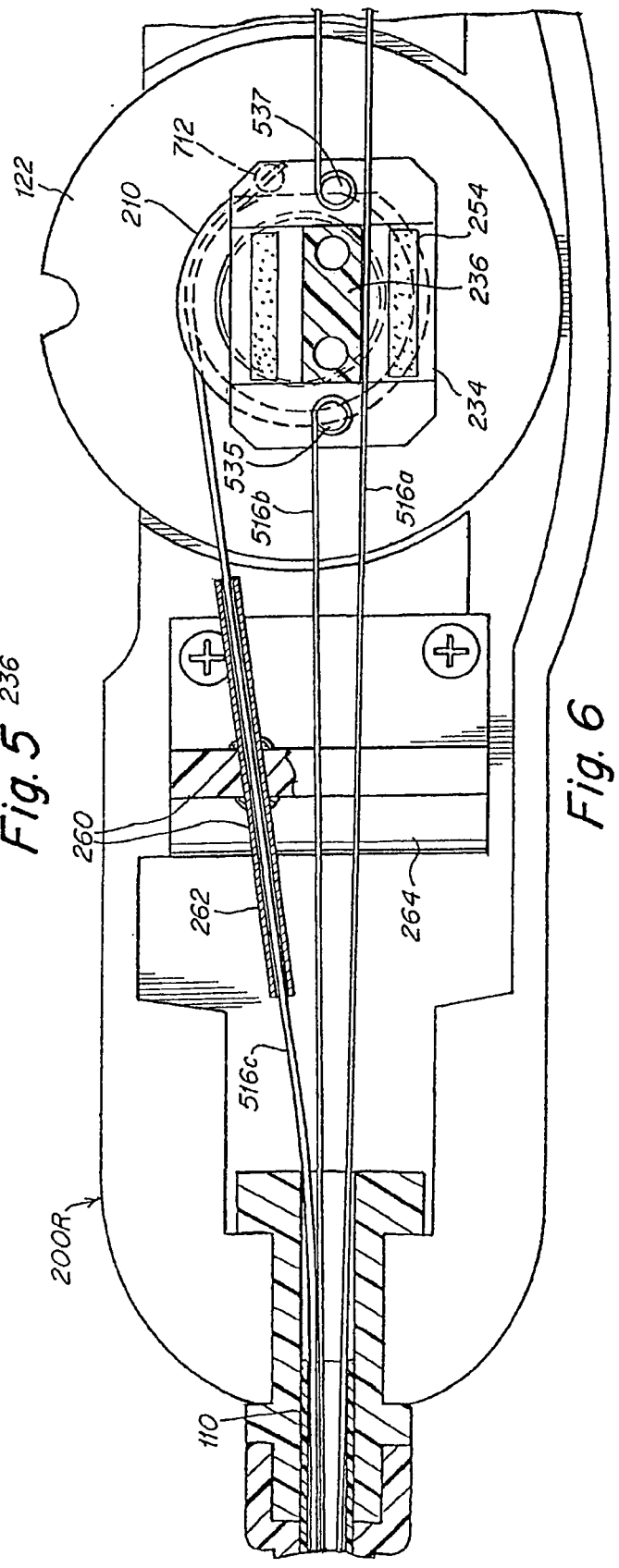

HANDLE DESIGN FOR A MEDICAL CATHETER

CROSS REFERENCE TO RELATED APPLICATIONS

This application claims the benefit of U.S. provisional application Ser. No. 60/287,057, entitled "Handles For Medical Devices," filed Apr. 27, 2001, which is incorporated herein by reference in its entirety.

BACKGROUND OF THE INVENTION

1. Field of the Invention

The present invention relates to handles for use with catheters, and more particularly to handles for use with electrophysiology catheters that are used in performing endocardial mapping and/or ablation procedures.

2. Discussion of the Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

In some individuals, the electrical impulses of the heart develop an irregular propagation, disrupting the heart's normal pumping action. The abnormal heartbeat rhythm is termed a "cardiac arrhythmia." Arrhythmias may occur when a site other than the sinoatrial node of the heart is initiating rhythms (i.e., a focal arrhythmia), or when electrical signals of the heart circulate repetitively in a closed circuit (i.e., a reentrant arrhythmia).

Techniques have been developed which are used to locate cardiac regions responsible for the cardiac arrhythmia, and also to disable the short circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel and into an endocardial site, and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice.

Current understanding is that atrial fibrillation is frequently initiated by a focal trigger from the orifice of or within one of the pulmonary veins. Though mapping and ablation of these triggers appears to be curative in patients with paroxysmal atrial fibrillation, there are a number of limitations to ablating focal triggers via mapping and ablating the earliest site of activation with a "point" radiofrequency lesion. One way to circumvent these limitations is to determine precisely the point of earliest activation. Once the point of earliest activation is identified, a lesion can be generated to electrically isolate the trigger with a lesion; firing from within those veins would then be eliminated or unable to reach the body of the atrium, and thus could not trigger atrial fibrillation.

Another method to treat focal arrhythmias is to create a continuous, annular lesion around the ostia (i.e., the openings) of either the veins or the arteries leading to or from the atria thus "corralling" the signals emanating from any points distal to the annular lesion. Conventional techniques include applying multiple point sources around the ostia in an effort to create such a continuous lesion. Such a technique is relatively involved, and requires significant skill and attention from the clinician performing the procedures.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete 'fence' around a circuit or tissue region is not always required in order to block the propagation of the arrhythmia; in many cases simply increasing the propagation path length for a signal may be sufficient. Conventional means for establishing such lesion 'fences' include a multiplicity of point-by-point lesions, dragging a single electrode across tissue while delivering energy, or creating an enormous lesion intended to inactivate a substantive volume of myocardial tissue.

SUMMARY OF THE INVENTION

The present invention encompasses handles that may be used with a catheter, and more particularly with an electrophysiology catheter for mapping electrical activity within the heart. The present invention also encompasses handles that may be used with an electrophysiology catheter to create lesions in the heart tissue (ablating), thereby creating a region of necrotic tissue which serves to disable the propagation of errant electrical impulses caused by an arrhythmia.

According to one aspect of the present invention, a handle for use with a catheter is provided. The handle comprises a housing, a cable, and a guide. The housing has a proximal end, a distal end, and a longitudinal axis that extends from the proximal end of the housing to the distal end of the housing. The cable is disposed in the housing and extends through the proximal end of the housing. A portion of the cable that is disposed in the housing is movable, under compression, in a first direction that is substantially aligned with the longitudinal axis of the housing. The guide is disposed in the housing and is adapted to prevent the portion of the cable from moving in a second direction that is transverse to the first direction when the portion of the cable is moved in the first direction.

According to another aspect of the present invention, a handle for use with a catheter is provided. The handle comprises a housing having a proximal end, a distal end, and a longitudinal axis that extends from the proximal end of the housing to the distal end of the housing, and a cable, disposed in the housing, that extends through the proximal end of the housing. A portion of the cable that is disposed in the housing is movable, under compression, in a first direction that is substantially aligned with the longitudinal axis of the housing. The handle further comprises means for preventing the portion of the cable from moving in a second direction that is transverse to the first direction when the portion of the cable is moved in the first direction.

According to a further aspect of the present invention, a method of using a catheter having a handle is provided. The handle has a proximal end, a distal end, and a longitudinal axis that extends from the proximal end of the handle to the distal end of the handle. The method comprises acts of applying a compressive force to a portion of a cable that is disposed in the handle to move the portion of the cable in a first direction that is substantially aligned with the longitudinal axis of the handle, and preventing the portion of the cable from moving in a second direction that is transverse to the first direction in response to the act of applying.

According to another aspect of the present invention, a handle for use with a catheter having an elongated shaft is provided. The handle includes a housing, a cable, and an actuator. The handle has a proximal end and a distal end, the distal end of the housing being attached to a proximal end of the elongated shaft. The cable is disposed in the housing and extends through the distal end of the housing and into the elongated shaft. The actuator is attached to the housing and the cable, and is movable between a first position in which the cable extends a first distance into the elongated shaft and a second position in which the cable extends a second distance into the elongated shaft, the second distance being less than the first distance. The handle further includes a guide, disposed in the housing, that is adapted to maintain a portion of the cable that is disposed between the distal end of the housing and the actuator when the actuator is in the second position in a substantially fixed lateral position when the actuator is moved toward the first position.

According to a further aspect of the present invention, a handle for use with a catheter having an elongated shaft is provided. The handle includes a housing, a cable, and an actuator. The handle has a proximal end and a distal end, the distal end of the housing being attached to a proximal end of the elongated shaft. The cable is disposed in the housing and extends through the distal end of the housing and into the elongated shaft. The actuator is attached to the housing and the cable, and is movable between a first position in which the cable extends a first distance into the elongated shaft and a second position in which the cable extends a second distance into the elongated shaft, the second distance being less than the first distance. The handle further includes guide means, disposed in the housing, for maintaining a portion of the cable that is disposed between the distal end of the housing and the actuator when the actuator is in the second position in a substantially fixed lateral position when the actuator is moved toward the first position.

According to yet another aspect of the present invention, a method for use with a catheter having an elongated shaft and a handle is provided. The handle includes a housing having a proximal end that is attached to a proximal end of the elongated shaft, a cable that is disposed in the housing and extends through the distal end of the housing and into the elongated shaft, and an actuator that is attached to the housing and the cable. The method comprises steps of moving the actuator from a first position in which the cable extends a first distance into the elongated shaft to a second position in which the cable extends a second distance into the elongated shaft, the second distance being greater than the first distance, and maintaining a portion of the cable that is disposed between the distal end of the housing and the actuator when the actuator is in the first position in a substantially fixed lateral position as the actuator is moved toward the second position.

BRIEF DESCRIPTION OF THE DRAWINGS

Illustrative, non-limiting embodiments of the present invention are described by way of example with reference to the accompanying drawings, in which:

FIG. 2 is an exposed side view of a handle for a mapping and/or ablation catheter according to one embodiment of the present invention;

FIG. 3 is an exposed top view of a section of the handle of FIG. 2 taken along line 3-3 in FIG. 2;

FIG. 5 is an exposed side view of a handle for a mapping and/or ablation catheter according to another embodiment of the present invention;

FIG. 6 is an exposed-top view of a section of the handle of FIG. 5 taken along line 6-6 in FIG. 5 according to one embodiment of the present invention;

DETAILED DESCRIPTION

In the follow description, the invention will be explained with particular reference to an electrophysiology catheter. However, the present invention is not so limited, and may be applied to any device where control of lateral cable movement is advantageous.

System Overview

Figure 1:
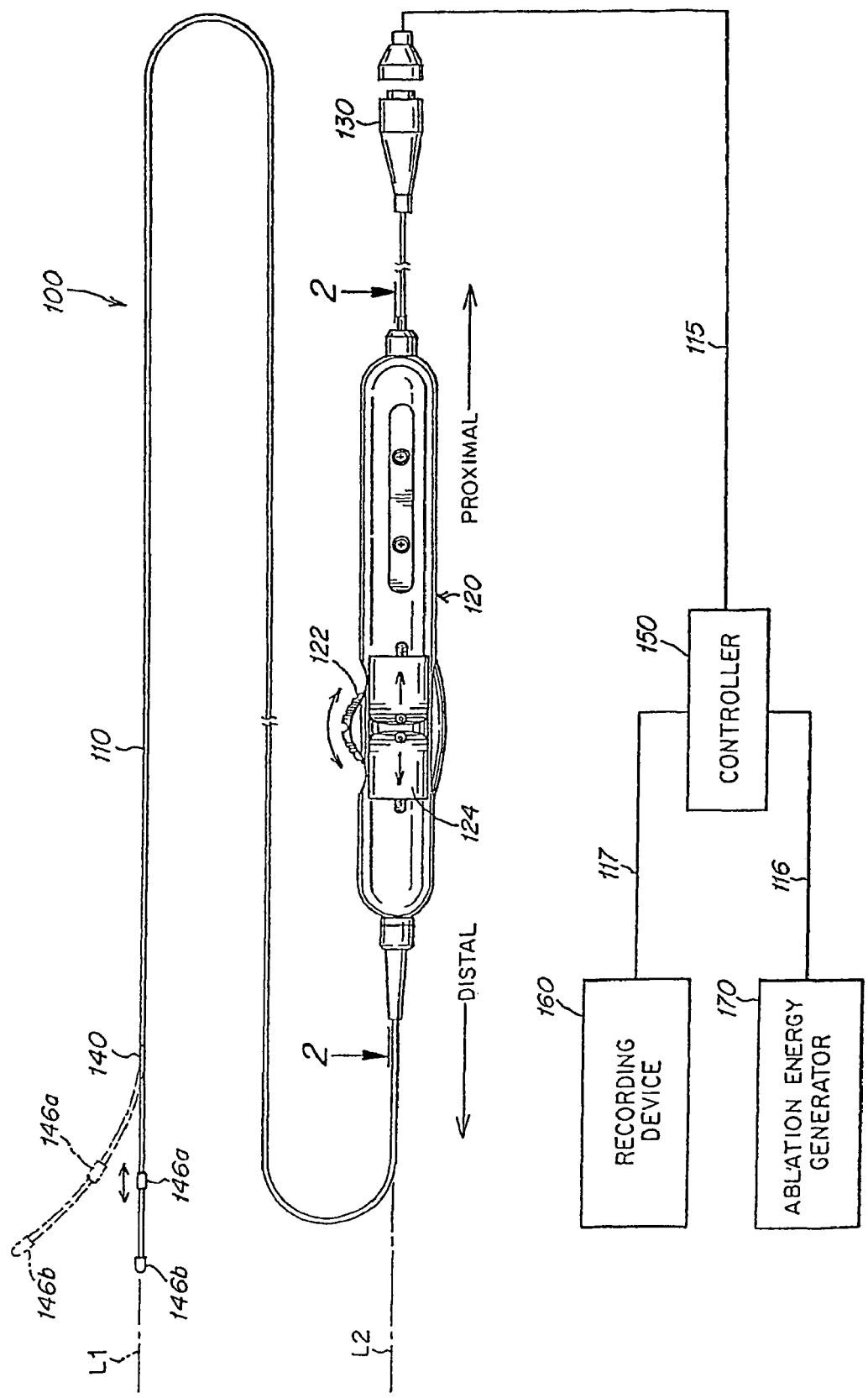
FIG. 1 illustrates a schematic view of a mapping and/or ablation catheter system in accordance with the present invention.

Reference is now made to FIG. 1, which illustrates an overview of a mapping and/or ablation catheter system for use in electrophysiology procedures, in accordance with one embodiment of the present invention. The system includes a catheter 100 having a flexible shaft 110, a control handle 120, and a connector 130. When used in mapping applications, the connector 130 is used to allow signal wires running from one or more mapping electrodes at a distal end of the catheter 100 to be connected to a device for recording signals, such as a recording device 160. When used in ablation applications, connector 130 is used to allow signal wires running from ablation electrodes at the distal end of the catheter 100 to be connected to a device for generating ablation energy, such as ablation energy generator 170.

A controller 150 is electrically connected to connector 130 via cable 115. In one embodiment, controller 150 may be a QUADRAPULSE RF CONTROLLER™ device available from C.R. Bard, Inc., Murray Hill, N.J. Ablation energy generator 170 may be connected to controller 150 via cable 116. Recording device 160 may be connected to controller 150 via cable 117. When used in an ablation application, controller 150 is used to control ablation energy, provided by ablation energy generator 170, to catheter 100. When used in a mapping application, controller 150 is used to process signals from catheter 100 and provide these signals to recording device 160. Although illustrated as separate devices, recording device 160, ablation energy generator 170, and controller 150 may be incorporated into a single device. It should further be appreciated that although both ablation energy generator 170 and recording device 160 are illustrated in FIG. 1, either or both of these devices may be incorporated in the catheter system in accordance with the present invention.

In this description, various aspects and features of the present invention will be described. The various aspects and features are discussed separately for clarity. One skilled in the art will appreciate that the features may be selectively combined in a device depending on the particular application. Furthermore, any of the various features may be incorporated in a catheter and associated method of use for mapping and/or ablation procedures.

Catheter Overview

As noted above, electrophysiology catheters such as the catheter 100 illustrated in FIG. 1 generally include a flexible shaft 110, a control handle 120, and a connector 130. The distal end 140 of the catheter 100 generally includes one or more electrodes 146a, 146b that may be used for mapping and/or ablation. The electrodes 146a, 146b are typically connected to signal wires extending along a length of the shaft 110, which are, in turn electrically connected to connector 130.

Frequently, one or more pull wires are also attached to a distal end 140 of the catheter 100 to control the distal end 140 of the catheter 100. The pull wires extend from the distal end 140 of the catheter along the length of the shaft 110 with the proximal end of the pull wires typically being attached to one or more actuators 122, 124 that are disposed on the handle 120. The actuators 122, 124 may be used for a variety of purposes, such as steering of the distal end 140 of the catheter 100 in one or more directions, controlling movement of a movable element (e.g., a movable electrode or a movable braided conductive mesh) disposed on the distal end 140 of the catheter 100, adjusting a radius of curvature of a distal end 140 of the catheter 100, etc.

For example, U.S. Pat. Nos. 5,383,852, 5,462,527, and 5,611,777 hereinafter referred to as the '852, '527, and '777 patents), which are incorporated herein by reference, illustrate various embodiments of a control handle that may be used for steering an electrophysiology catheter. Commonly assigned and co-pending PCT application entitled ELECTROPHYSIOLOGY CATHETER FOR MAPPING AND/ OR ABLATION, filed Mar. 29, 2002 (hereinafter referred to as the PCT application), which is incorporated herein by reference, illustrates various embodiments of a control handle that may be used for adjusting a radius of curvature of an arcuately curved distal tip portion of the catheter, for moving a movable electrode along a length of the arcuately curved distal tip portion of the catheter, for controlling steering of the arcuately curved distal tip portion of the catheter, and for actively bending the arcuately curved distal tip portion of the distal end of the catheter so that the arcuate curve is oriented in a plane that is approximately perpendicular to a longitudinal axis (L1 of FIG. 1) of the shaft of the catheter. Moreover, co-pending and commonly assigned U.S. patent application Ser. No. 09/845,022, entitled APPARATUS AND METHODS FOR MAPPING AND ABLATION IN ELECTROPHYSIOLOGY PROCEDURES, filed Apr. 27, 2001 (hereinafter referred to as the co-pending application), which is incorporated herein by reference, illustrates various embodiments of a control handle that may be used to deploy (i.e., radially expand) and un-deploy (i.e., collapse) a braided conductive mesh that is disposed at the distal end of the catheter.

In each of the above noted catheters, the wires that are used to control the distal end of the catheter are typically operable under tension (hence the term 'pull wire'), such that tension applied to the pull wire by movement of an actuator disposed on the handle results in movement of the distal end of the catheter, or movement of a movable element disposed on the distal end of the catheter. Frequently, the pull wires are associated in pairs, such that one pull wire of a pair controls movement of the distal end of the catheter (or movement of a movable element disposed on the distal end of the catheter) in a first direction, and the other pull wire of the pair controls movement of the distal end of the catheter (or movement of a movable element disposed on the distal end of the catheter) in a second direction, frequently opposite to the first direction. In general, except for when the actuator is in a neutral position, one pull cable of the pair of pull cables is in tension, and the other pull cable of the pair is not (i.e., is slack).

The Handle

Handles in accordance with the present invention are shown in FIGS. 2-7. In each of the illustrated embodiments, the handle includes a guide that permits a small diameter cable, for example only 0.011 inches in diameter, to be used in both tension and in compression. The guide acts to maintain a portion of the cable that is disposed within the handle in a substantially fixed lateral position within the handle as the cable is urged distally toward the proximal end of the shaft. The term "substantially fixed lateral position" is defined herein to mean that the portion of the cable that is disposed within the handle is prevented from moving, bending, or bowing in a direction transverse to the desired direction of movement of the cable. By maintaining the portion of the cable in a substantially fixed lateral position, the column strength of the cable is increased such that a compressive force applied to the cable by movement of an actuator attached to the cable is translated into distal movement of the cable. The distal movement of cable may be used for a myriad of different uses, as indicated above.

Figure 4:
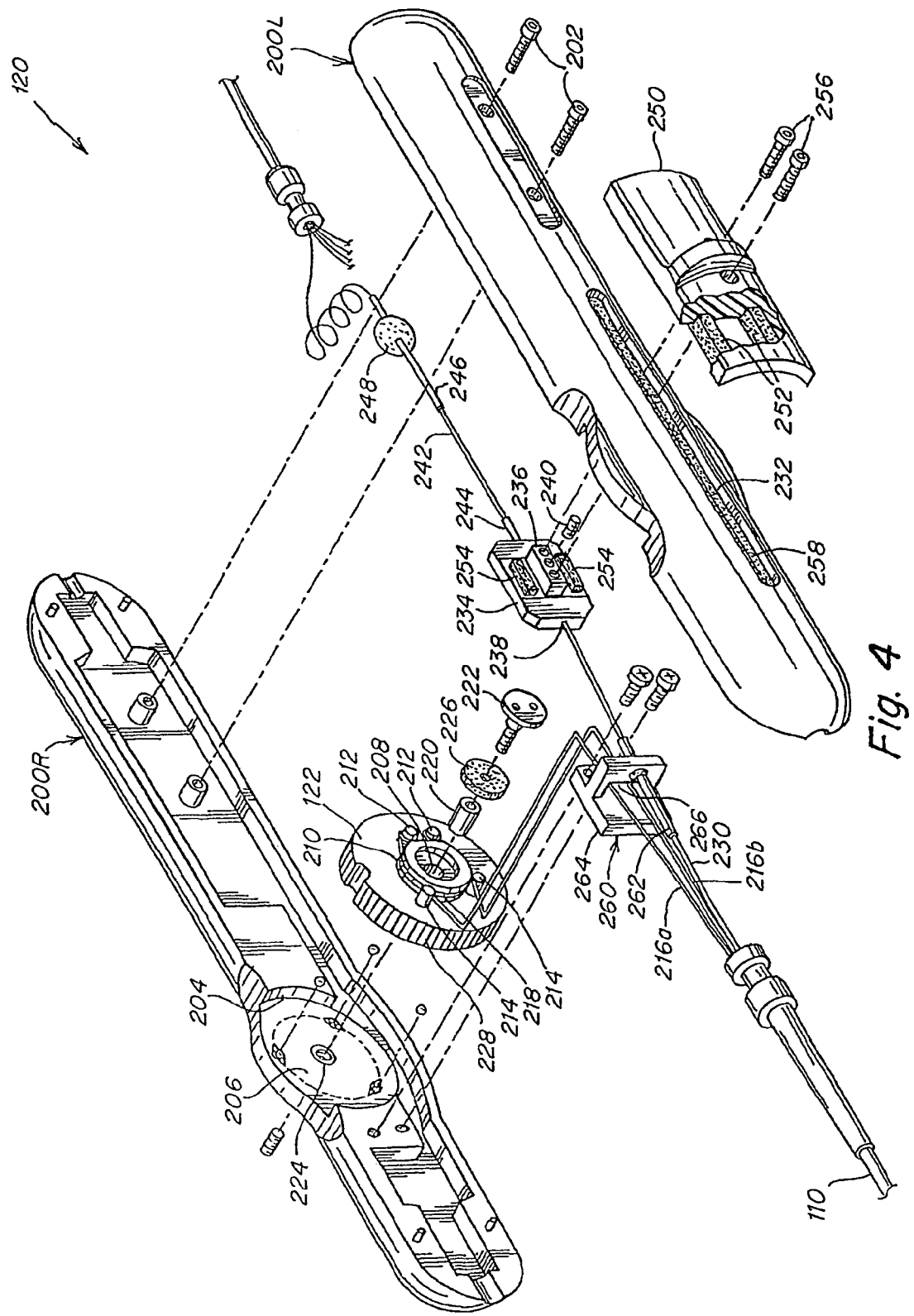
FIG. 4 is an exploded view of the handle of FIG. 2.

In the embodiment of FIGS. 2, 3, and 4, linear movement of a slide actuator 124 (FIG. 1) is used to move a portion of a cable that is disposed in the handle distally into and proximally out of the shaft 110 of the catheter 100. In the embodiment of FIGS. 5 and 6, rotary movement of a thumb wheel actuator 122 (FIG. 1) is used to move a portion of a cable that is disposed in the handle distally into and proximally out of the shaft 110 of the catheter 100, and in the embodiment of FIG. 7, rotary movement of the thumb wheel actuator 122 is used to move respective portions of two different cables that are disposed in the handle distally into and proximally out of the shaft 110 of the catheter 100. Advantageously, in each of these embodiments, a single cable may used in both tension and compression. Although not limited to any specific use, the single cable may be used to control steering of the distal end 140 of the catheter 100, to control movement of a movable element (e.g., a movable electrode or a movable braided conductive mesh) disposed on the distal end 140 of the catheter 100, to adjust a radius of curvature of an arcuately curved distal tip portion of the catheter, to control bending of an arcuately curved distal tip portion of the distal end of the catheter so that the arcuately curved distal tip portion is oriented in a plane that is approximately perpendicular to a longitudinal axis of the shaft of the catheter, etc.

Referring to FIGS. 2-4, a handle according to a first embodiment of the present invention is described. The handle 120 comprises a housing having a left section 200L and a right section 200R. These two sections 200L and 200R are somewhat semicircular in cross section and have flat connecting surfaces which may be secured to each other, for example, by screws 202, along a common plane to form a complete housing for the handle 120. The outer surfaces of the handle 120 are contoured to be comfortably held by the user.

A wheel cavity 204 is formed within the right section 200R of the handle 120.

The wheel cavity 204 includes a planar rear surface 206 which is generally parallel to the flat connecting surface of the handle 120. The thumb wheel actuator 122 is a generally circular disc having a central bore 208, an integrally formed pulley 210, and upper and lower cable anchors 212. Upper and lower cable guides 214 serve to retain pull cables 216a and 216b within a guide slot or groove 218 formed in a surface of the integrally formed pulley 210. The pull cables 216a and 216b may be used for a variety of purposes, such as for steering of the distal end of the catheter. For example, as described in the '852, '527, and '777 patents, the distal ends of the pull cables 216a, 216b may extend through the shaft 110 and be connected to the distal end 140 of the catheter at an off-axis location, whereby tension applied to one or more of the pull wires causes the distal portion of the catheter to curve in a predetermined direction or directions.

In the embodiment illustrated, the thumb wheel 122 rotates about a sleeve 220 inserted in the central bore 208. The thumb wheel 122 is held in position by a shoulder nut 222 that mates with a threaded insert 224 in the planar rear surface 206 of the right section 200R of the handle 120. To provide friction that permits the thumb wheel to maintain its position even when tension is applied to one of the cables 216a, 216b, a friction disk 226 is provided between the shoulder nut 222 and the thumb wheel 122. Tightening of the shoulder nut 222 increases the amount of friction applied to the thumb wheel 122.

A peripheral edge surface 228 of the thumb wheel 122 protrudes from a wheel access opening so that the thumb wheel 122 may be rotated by the thumb of the operator's hand which is used to grip the handle 120. To ensure a positive grip between the thumb wheel 122 and the user's thumb, the peripheral edge surface 228 of the thumb wheel 122 is preferably serrated, or otherwise roughened. Different serrations on opposite halves of thumb wheel 122 enable the user to "feel" the position of the thumb wheel.

The left section 200L of the handle 120 supports part of the mechanism for applying tensile and compressive forces to the cable 230. As will be described in detail further below, tensile and compressive force may be applied to cable 230 via the slide actuator 122 (FIG. 1) to move the portion of the cable 230 that is disposed within the handle proximally and distally within the handle 120. Where a distal end of the cable 230 is attached to a distal end of the catheter, movement of the slide actuator proximally and distally along the handle may be used to steer the catheter, or to control a radius of curvature of an arcuately curved tip assembly that is attached to the distal end of the catheter as described in the aforementioned PCT application. Alternatively, movement of the slide actuator proximally and distally along the handle may be used to actively bend a tip assembly this is attached to a distal end of the catheter so as to orient an arcuately curved portion of the tip assembly in a plane that is approximately perpendicular to a longitudinal axis of the shaft and then return the arcuately curved portion of the tip assembly to its original orientation. Alternatively still, where the distal end of the cable is attached to a movable element that disposed on the distal end of the catheter, movement of the slide actuator proximally and distally may be used to move the movable element proximally and distally along a length of the distal end of the catheter.

To accommodate the protruding portion of the thumb wheel 122, the left handle section 200L includes a wheel access opening similar in shape to the wheel access opening of the right handle section 200R. It also includes an elongated slot 232 in its side surface. A slider 234 is provided with a neck portion 236 which fits snugly within the slot 232. The slider 234 includes a bore 238 to receive a proximal end of the cable 230. The proximal end of the cable 230 is inserted into the bore 238 and held in place by a set screw 240. The proximal end of the cable may additionally or alternatively be secured within the bore 238 using an epoxy.

According to the embodiment illustrated in FIG. 4 in which cable 230 is used to conduct electrical signals from the distal end of the catheter (e.g., to conduct electrical signals from a movable electrode or a braided conductive mesh), the electrically insulating coating of the cable 230 is removed prior to inserting the cable into the bore 238 of the slider. In this embodiment, a signal wire 242 is soldered to the stripped proximal end of the cable 230 and the soldered electrical connection is covered by an insulating shield or cover 244. The insulating shield or cover 244 reduces electrical interference and prevents short circuiting with any other signal wires. A second insulating shield or cover 246 is placed about signal wire 242 and secured in place, for example with expoxy 248 in a proximal portion of the right section of the handle 200R. Although the second insulating cover 248 is epoxied in place, the signal wire 242 is pennitted to move proximally and distally within the second insulating cover 248. The proximal end of signal wire 242 may be electrically connected to the connector 130 (FIG. 1). Further, a sufficient amount of excess wile is provided to allow for such movement of the signal wire 242. It should be appreciated that the cable 230 may alternatively extend to the connector 130, such that the signature 242 is omitted.

A slider grip 250 is attached to the neck portion 236 of the slider 234 and positioned externally of the handle 120. The slider grip 250 is preferably ergonomically shaped to be comfortably controlled by the user. Together, the slider 234 and the slider grip 250 form the slide actuator 124 depicted in FIG. 1. Preload pads 252 are positioned between the outer surface of the left handle section 200L and the slider grip 250. By tightening the screws 256 that attach the slider grip 250 to the slider 234, friction may be applied to the slider 234 and thus, to the cable 230. Preload pads 254 may also be placed on a surface of the slider 234 for a similar purpose.

A dust seal 258 having an elongated slit and preferably made from latex is bonded along the slot 232 within the left handle section 200L. The neck portion 236 of the slider 234 protrudes through the slit of the dust seal 258 so that the slit only separates adjacent to the neck portion 236. Otherwise, the slit remains "closed" and functions as an effective barrier preventing dust, hair and other contaminants from entering the handle 120. Additional details of the handle 120 are described in '852, '527, and '777 patents, as well as in the PCT application and the co-pending application.

According to an embodiment of the present invention, a cable guide 260 is attached to the right handle section 200R and used to maintain the portion of the cable 230 that is disposed within the handle 120 in a substantially fixed lateral position within the handle as the slider 124 is moved distally and proximally along the handle 120. In the illustrated embodiment, this substantially fixed lateral position is generally aligned with a longitudinal axis (L2) in FIG. 1 of the handle 120 and the proximal end of the shaft 110. In the illustrated embodiment, the guide 260 includes a cylindrical mandrel 262 and a retainer 264, although it should be appreciated that the guide may be integrally formed within the left and right handle sections 200L and 200R. As illustrated, the retainer 264 includes a bore to receive the mandrel 262 and may also include a slot 266 to guide the cables 216a, 216b that are attached to the thumb wheel 122 and prevent their entanglement with one another.

The mandrel 262 may be formed from any suitable material, for example, from stainless steel hypodermic tubing, that is sufficiently stiff to prevent the cable from bowing in a direction that is orthogonal (i.e., lateral) to a longitudinal axis (22) of the handle 120. The mandrel 262 has an inner diameter that is slightly greater than an outer diameter of the cable 230, and has a length that is approximately twenty percent or more than a length of the portion of the cable that is disposed within the handle when the slider 234 is in its most proximal position. It should be appreciated that the mandrel need not be cylindrical in shape, as other shapes may be used, so long as they are capable of preventing movement of the cable 230 in a lateral direction.

It should be appreciated that the length of the mandrel 262 may vary depending upon the dimensions of the handle 120 and the desired amount of movement of the cable 230 proximally and distally within the handle 120. In general, the mandrel 262 should be sufficiently long to prevent the cable 230 from bending in a direction that is transverse (i.e., lateral) to the desired direction of movement of the cable 230 as a compressive force is imparted to the cable 230 via the slide actuator 124. As shown, the mandrel 262 is positioned within the retainer so that the portion of the mandrel 262 that is distal of the retainer 264 is longer than the portion that is proximal of the retainer 264. This permits the slider 234 to have a sufficient amount of travel (e.g., approximately one inch) between its farthest proximal and distal positions.

Where the mandrel 262 is formed from a straight cylindrical member, and the portion of the cable 230 that is fixed in position within the slider 234 is not aligned with the longitudinal axis of the proximal end of the shaft (for example, is at a different elevation than the proximal end of the shaft), the mandrel 262 should preferably terminate prior to the proximal end of the shaft 110 to permit the cable 230 to bend slightly prior to entering the proximal end of the shaft. Where the portion of the cable 230 that is fixed in position within the slider 234 is aligned with the longitudinal axis of the proximal end of the shaft 110, or where the mandrel 262 is shaped so as to guide the cable 230 into the proximal end of the shaft 110 along the longitudinal axis of the proximal end of the shaft, the mandrel 262 may terminate just distally of the proximal end of the shaft 110.

In one embodiment, the cylindrical mandrel has an inner diameter of approximately 0.025-0.030 inches, and a length of approximately $3/4^{th}$ of an inch. In this embodiment, the portion of the mandrel 262 that is disposed distally of the retainer 264 is approximately 0.5 inches in length. Applicant has found that the above dimensions permit a stainless steel cable 230 having an outer diameter of approximately 0.020 inches to be used with the catheter 100 while imparting a sufficient column strength to the cable 230 to permit it to drive the cable 230 in compression distally along a length of the shaft 110. The cable 230 is preferably ground to have an outer diameter of approximately of approximately 0.011 inches just prior to where it enters the shaft 110 of the catheter 100, to reduce the overall outer diameter of the catheter shaft 110. Despite the reduced diameter of the cable 230 that is within the shaft 110 of the catheter 100, the outer casing of the catheter shaft prevents movement of the cable in a direction other than distally along the length of the shaft 110. It should be appreciated that the very distal end of the cable 230 may also be ground to an even smaller outer diameter to further reduce the overall outer diameter of the distal end 140 of the catheter 100.

In another embodiment, the cylindrical mandrel has an inner diameter of approximately 0.055-0.060 inches, a length of approximately $3/4^{th}$ of an inch, and the length of the portion of the mandrel 262 that is disposed distally of the retainer 264 is again approximately 0.5 inches in length. In this embodiment, a stainless steel cable 230 having an outer diameter of approximately 0.050 inches is used, with the outer diameter of the cable 230 being ground to approximately 0.020 inches where the cable 230 enters the catheter shaft 110, and being ground to an outer diameter of approximately 0.011 inches at the distal end 140 of the catheter. It should be appreciated that other dimensions for the various portions of the cable 230 may alternatively be used, depending upon the intended application.

It should also be appreciated that, rather than grounding cable 230 to varying diameters, a small diameter (e.g., 0.050 inches or less in outer diameter) piece of hypodermic tubing may alternatively be used. For example, rather than having the cable 230 extend all the way to the slide actuator 122, the proximal end of the cable 230 may be soldered within a small diameter piece of hypodermic tubing just prior to where the cable 230 enters the shaft 110 of the catheter, with the hypodermic tubing then being attached to the slide actuator 122. This alternative manner of construction avoids the grinding of a significant length of the cable 230 that may be desired to reduce the overall outer diameter of the shaft 110 of the catheter. Any grinding that was desired to be done to the distal end of the cable 230 to further the outer diameter of the distal end 140 of the catheter would then be limited to the relative small length of the distal end of the cable 230.

Alternatively still, rather than the proximal end of the cable 230 terminating just prior to where the cable 230 enters the shaft 110, and being soldered or otherwise affixed to a distal end of the hypodermic tubing, the cable 230 may extend to and past the slide actuator. The hypodermic tubing could then be soldered in position around the portion of the cable that is within the handle, to prevent that portion of the cable 230 from moving in a transverse direction under compression. The slider may then be attached to both the hypodermic tubing and the cable 230 which is soldered or otherwise fixed (e.g., by an epoxy) therein. Other suitable types of construction will of course be appreciated by those skilled in the art, as the present invention is not limited to a particular construction of the cable 230.

Figure 7:
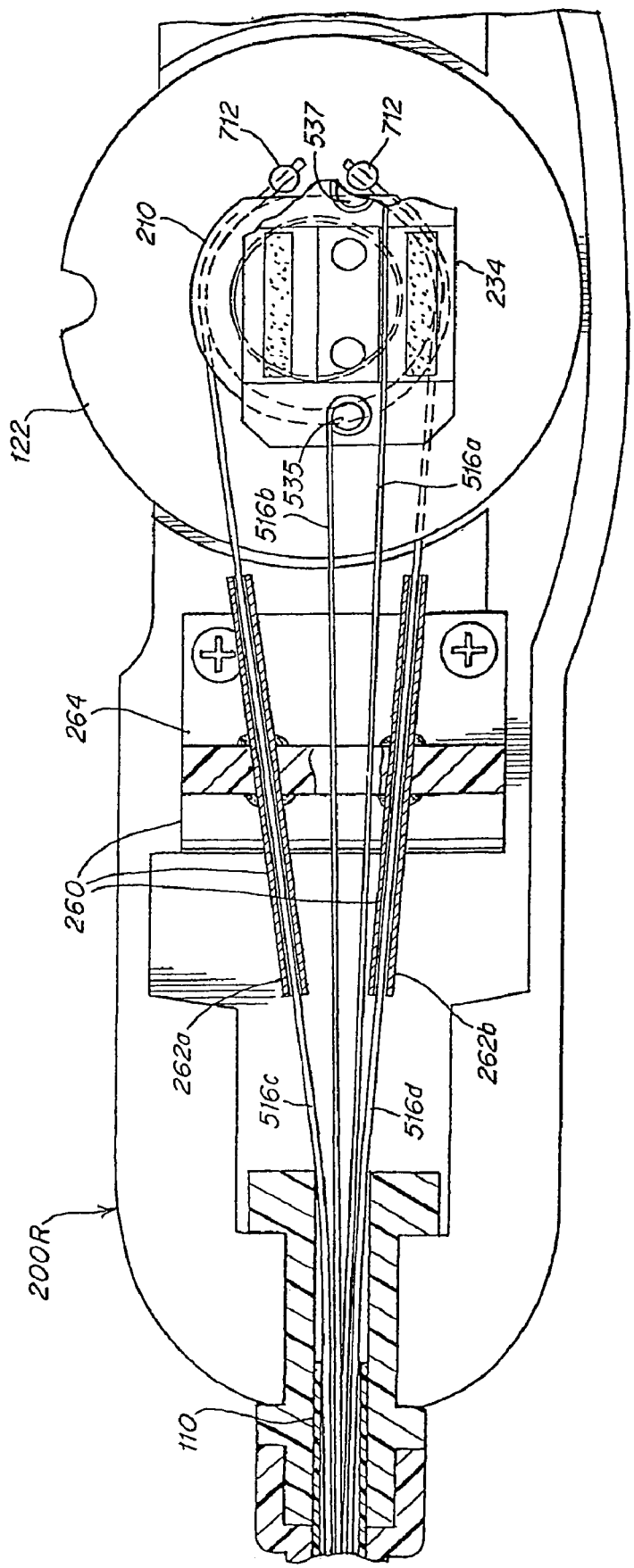
FIG. 7 is an exposed top view of a section of the handle of FIG. 5 taken along line 7-7 in FIG. 5 according to another embodiment of the present invention.

FIGS. 5 and 6 illustrate alternative embodiments of the present invention in which rotary movement of a thumb wheel actuator 122 (FIG. 1) is used to move a portion of a cable that is disposed in the handle 120 distally into and proximally out of the shaft 110 of the catheter 100, and FIG. 7 illustrates yet another alternative embodiment in which rotary movement of the thumb wheel actuator 122 is used to move respective portions of two different cables that are disposed in the handle 120 distally into and proximally out of the shaft 110 of the catheter 100. As each of the handles illustrated in FIGS. 5, 6, and 7 share many of the same elements as the handle described with respect to FIGS. 2, 3, and 4, only those elements that differ from the embodiment of FIGS. 2, 3, and 4 are described in detail herein.

In the embodiments illustrated in FIGS. 5, 6, and 7, rather than securing a single cable 230 that is used in both tension and compression, the slider 234 includes a forward cable anchor 535 and a rear cable anchor 537 for anchoring respective pull cables 516a and 516b. Pull cable 516b is directly attached to a forward cable anchor 535 on the slider 234 and becomes taught when the slider 234 is moved toward the distal end of the handle 120. Pull cable 516a is guided by a return pulley 505 prior to being attached to a rear cable anchor 537 on the slider 234 and becomes taught when the slider 234 is moved toward the proximal end of the handle 120. The return pulley 505 is rotatably attached to a pulley axle (not shown) which is supported in the right handle section 200R. The return pulley 505 may include a groove (not shown) to guide pull cable 516a. The pull cable 516a and 516b may be used for a variety of purposes, for example, steering the distal end of the catheter. Further details of the construction and operation of the slider 234 are described in the '852, '527, and '777 patents, as well as the PCT application.

In the embodiment depicted in FIGS. 5 and 6, the cable guide 260 is again attached to the right handle section 200R. However, in the embodiment depicted in FIGS. 5 and 6, the cable guide 260 is used to maintain the portion of a cable 516c that is disposed within the handle 120 and attached to the thumb wheel 122 in a substantially fixed lateral position as the thumb wheel 122 is rotated clockwise and counter clockwise. Details of one implementation of the thumb wheel that may be used with this embodiment are described further below with reference to FIGS. 8, 9, and 10.

Rotation of the thumb wheel 122 in a clockwise direction (in FIG. 6) moves the cable 516c in a proximal direction as tension is applied to the cable 516c via the thumb wheel 122, and rotation of the thumb wheel 122 in a counterclockwise direction moves the cable 516c in a distal direction as a compressive force is applied to the cable 516c via the thumb wheel 122. Cable guide 260 maintains the cable 516c in a substantially fixed lateral position within the handle as the thumb wheel is rotated. The cable 516c may be used for a variety of purposes, for example, for steering or for moving a movable element proximally and distally along a length of the distal end of the catheter. Advantageously, a single cable may be used in both tension and compression. It should be appreciated that because only a single cable can be used for movement in two different directions, a lesser number of cables may be included in the shaft of the catheter without any loss in functionality, thereby permitting a reduction in the outer diameter of the shaft of the catheter. Further, because of the increased column strength of the cable imparted by the guide 260, relatively small diameter cables may be used, permitting a further reduction in the outer diameter of the shaft of the catheter.

In the illustrated embodiment, the guide 260 again includes a cylindrical mandrel 262 and a retainer 264, although it should again be appreciated that the guide 260 may be integrally formed within the left and right handle sections 200L and 200R. It should again be appreciated that the mandrel need not be cylindrical in shape, as other shapes may be suitably employed. As in the embodiment of FIGS. 2-4, the retainer 264 includes a bore to receive the mandrel 262. The retainer 264 may also include a slot, or apertures, or grooves to guide the cables 516a, 516b that are attached to the slide actuator 124 and prevent their entanglement with one another. The mandrel 262 may be formed from any suitable material, for example, from stainless steel hypodermic tubing, that is sufficiently stiff to prevent the bending of the cable 516c as the thumb wheel 122 is rotated. As in the previously described embodiment of FIGS. 2-4, the inner diameter of the mandrel 262 is slightly larger than the outer diameter of the cable 516c.

In general, the length of the mandrel 262 depicted in FIGS. 5 and 6 may be longer that that described above with respect to FIGS. 24, as the thumb wheel 122 is fixed in position along a length of the handle 120 and not movable relative thereto, like the slide actuator 124. Moreover, it should be appreciated that the proximal end of the mandrel 262 should be placed close to the position where the cable 516c separates from the integrally formed pulley 210 to prevent lateral bending of the cable 516c as the cable is urged distally by rotation of the thumb wheel 122. As shown, the mandrel 262 terminates at a distance that is spaced apart from the proximal end of the shaft 110 to permit the cable 516c to bend slightly prior to entering the proximal end of the shaft 110. It should be appreciated that the mandrel 262 may alternatively be shaped so as to guide the cable 516c into the proximal end of the shaft along the longitudinal axis of the proximal end of the shaft, such that the mandrel 262 may terminate just distally of the proximal end of the shaft.

The embodiment of the handle depicted in FIG. 7 is similar to the embodiment described above with respect to FIGS. 5 and 6. However, in the embodiment depicted in FIG. 7, the cable guide 260 is used to maintain respective portions of a pair of cables 516c, 516d that are disposed within the handle 120 and attached to the thumb wheel 122 in a substantially lateral fixed positions as the thumb wheel 122 is rotated clockwise and counter clockwise. Each of the cables 516c and 516d is anchored to the thumb wheel 122 by respective cable anchor 712.

Rotation of the thumb wheel 122 in a clockwise direction (in FIG. 7) moves the cable 516c in a proximal direction as a tensile force is applied to the cable 516c via the thumb wheel 122, and moves the cable 516d in a distal direction as a compressive force is applied to the cable 516d via the thumb wheel 122. Similarly, rotation of the thumb wheel 122 in a counterclockwise direction moves the cable 516c in a distal direction as a compressive force is applied to the cable 516c via the thumb wheel 122, and moves the cable 516d in a proximal direction as a compressive force is applied to the cable 516d via the thumb wheel 122. The cable guide 260 again maintains each of the cables 516c and 516d in a substantially fixed lateral position in both tension and compression.

The cables 516c and 516d may be used for a myriad of purposes as noted above, for example, for steering or for moving a movable element proximally and distally along a length of the distal end of the catheter. It should be appreciated that the cables 516c and 516d may operate in tandem, for example, with one cable (e.g., 516c) controlling movement of the distal end of the catheter in a first direction and the other cable (e.g., 516d) controlling movement of the distal end of the catheter in an opposite direction, or may be used to control different functions.

In the embodiment illustrated in FIG. 7, the guide 260 includes a pair of mandrels 262a, 262b and a retainer 264. It should be appreciated that the mandrels 262a, 262b need not be cylindrical, as other shapes may be suitably employed. As in the previously described embodiments, the guide 260 may alternatively be integrally formed within the left and right handle sections 200L and 200R, rather than separate therefrom. The retainer 264 includes a pair of bores to receive each of the mandrels 262a, 262b. The mandrels 262a, 262b may be formed from any suitable material, as described above with respect to FIGS. 2-6. Although not separately depicted, it should be appreciated that the handles described above with respect to FIGS. 5, 6, and 7 may alternatively be used with a slide actuator 124, such as that described with respect to FIGS. 2-4. That is, the slider 232 (FIGS. 2-4) may be used to control a single cable that is operable in both tension and compression, rather than a pair of pull cables 516a, 516b, and the thumb wheel 122 may be used to control one or a pair of cables, each of which is operable in both tension and compression.

Figure 8:
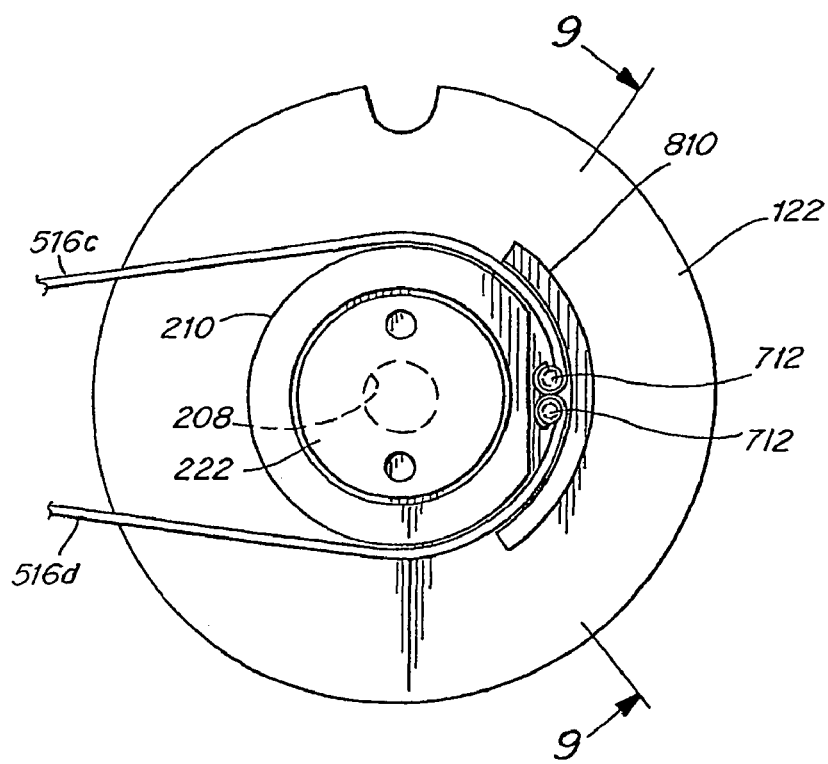
FIG. 8 is a top view of a thumb wheel actuator according to an embodiment of the present invention.
Figures 9, 10:
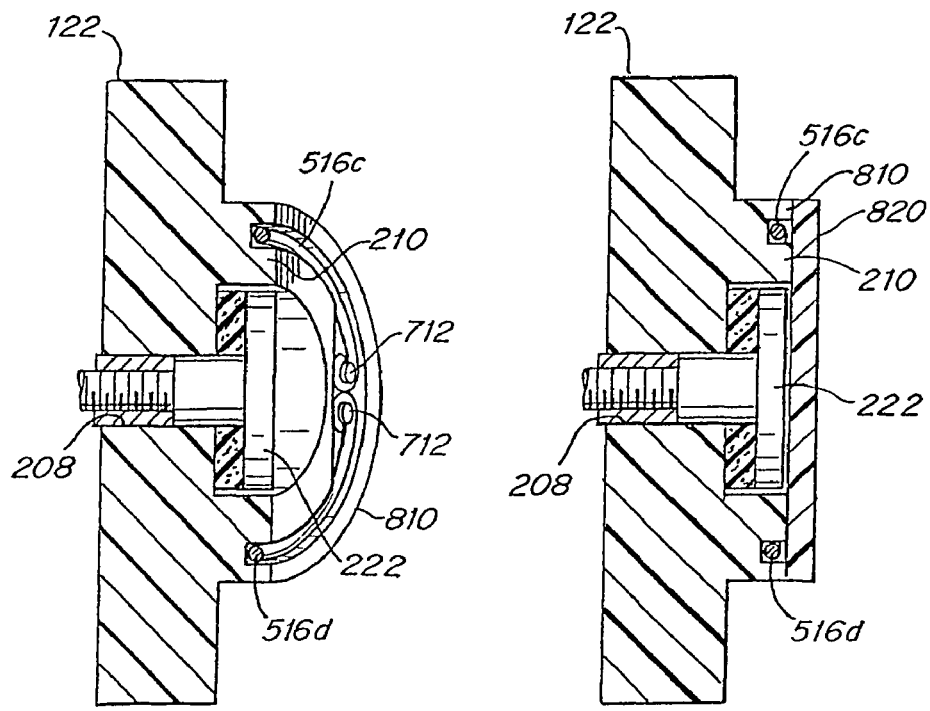
FIG. 9 is an elevational view of the thumb wheel actuator of FIG. 8.
FIG. 10 is a side view of the thumb wheel actuator of FIG. 8.

FIGS. 8-10 illustrate one implementation of a thumb wheel 122 that may be used with the embodiments of the handle 120 described above with reference to FIGS. 5-7.

As previously described, the thumb wheel 122 is a generally circular disc having a central bore 208, and an integrally formed pulley 210. However, in contrast to the thumb wheel 122 described with respect to FIGS. 2-4, surrounding a proximal portion of the pulley 210 is an arcuate wall 810. The arcuate wall 810 acts to prevent the cables 516c and 516d from bending away from the pulley as the thumb wheel 122 is rotated counterclockwise and clockwise, respectively. Upper and lower cable anchors 712 are disposed within the arcuate wall 810 and serve to attach the cables 516c, 516d to the thumb wheel 122. The arcuate wall 810 spans less than 180 degrees so that rotation of the thumb wheel 122 may be accomplished without the wall deflecting the cables 516c, 516d. For example, the thumb wheel 122 may be rotated approximately 45 degrees clockwise and approximately 45 degrees counter clockwise from a neutral position without the wall deflecting the cables 516d and 516c, respectively. A top cover 820 may be attached to the thumb wheel 122 to prevent the cables 516c, 516d from bending in an upward direction (FIG. 10), while the surface of the thumb wheel 122 itself prevents bending of the cables in a downward direction (FIG. 10).

Distal End Configurations

As noted above, embodiments of the present invention may be used for a variety of purposes, such as, for example: steering the distal end of the catheter in one or more directions, adjusting a radius of curvature of an arcuately curved distal tip portion of the catheter, moving a movable electrode along a length of the distal end of a catheter, or along arcuately curved distal tip portion of the catheter, controlling steering of an arcuatey curved distal tip portion of the catheter, actively bending an arcuately curved distal tip portion of the distal end of the catheter so that the arcuate curve is oriented in a plane that is approximately perpendicular to a longitudinal axis of the shaft of the catheter, or deploying and/or un-deploying a braided conductive mesh that is disposed at the distal end of the catheter.

Figure 11:
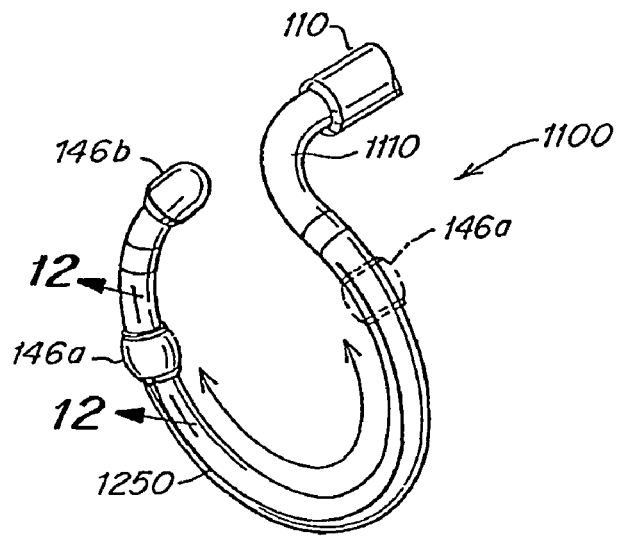
FIG. 11 is a perspective view of a distal end tip assembly that may be used with the catheter system of FIG. 1, and which includes a sliding electrode.
Figure 12:
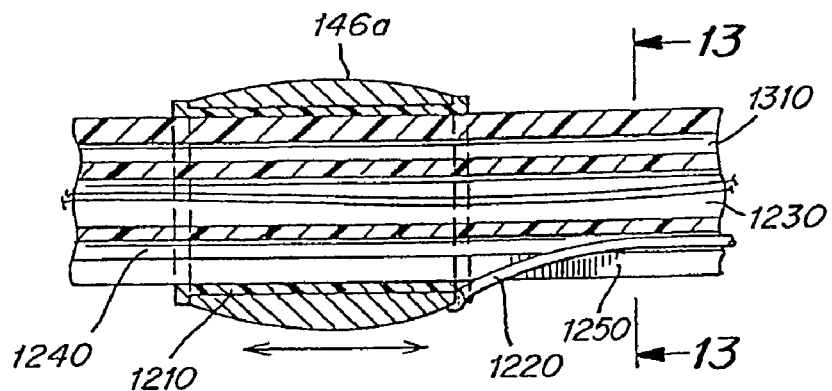
FIG. 12 is a cross sectional side view of the distal end tip assembly of FIG. 11 taken along line 12-12 in FIG. 11.
Figure 13:
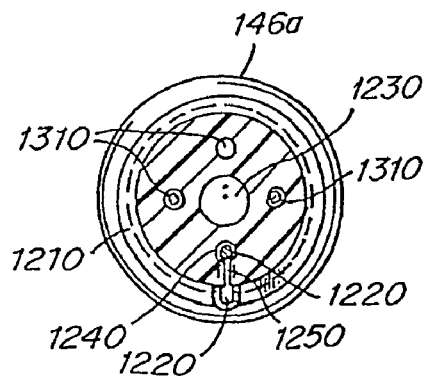
FIG. 13 is a cross sectional end view of the distal end of tip assembly of FIG. 11 taken along line 13-13 in FIG. 12.

FIGS. 11-13 illustrates a tip assembly 1100 that may be attached to a distal end of the shaft 110 of a catheter, such as the catheter 100 (FIG. 1) to control a movable electrode 146a that is disposed along a distal end of the tip assembly 1100. In the illustrated tip assembly, the distal end of the tip assembly 1100 is curved in an arcuate manner and the arcuate curve is oriented in a plane that is substantially perpendicular to a longitudinal axis of the shaft 110, such as described in the above referenced PCT application. The approximate ninety degree bend 1110 in the tip assembly may be an active bend or a fixed bend.

As shown in FIG. 11, the distal end of the tip assembly 1100 may include a movable electrode 146a that is movable between a first position and a second position spaced apart along a length of the distal end of the tip assembly 140. In the embodiment illustrated, the movable electrode 146a slides along a length of the distal end that spans approximately 360 degrees, and when used for ablation, may be used to form a circular lesion. The radius of curvature of the arcuate curve may be adjustable, as described in the aforementioned PCT application. The very distal end of the tip assembly 1100 may include a cap electrode 146b, or alternatively, the cap may be made from a non-conductive material and may simply serve to terminate the very distal end of the tip assembly 1100. Where a cap electrode 146b is used, an insulating spacer may be placed proximally of the cap electrode to prevent the movable electrode 146a from electrically contacting the cap electrode 146b.

As shown in FIG. 12, which is a cross sectional side view of the distal end of the tip assembly in FIG. 11 taken along line 12-12, the electrode 146a may be attached to a cylindrically-shaped plastic slider 1210 that that can slide back and forth along a length of the distal end of the tip assembly 1110. In the embodiment shown, the distal end of a metal push/pull cable 1220 is welded to an outer surface of the electrode 146a, with the proximal end of the push/pull 1220 cable being attached to an actuator 122, 124 on the handle 120. For example, the push/pull cable 1220 may be attached to the slider 234 as illustrated in FIGS. 2-4, or alternatively, the push/pull cable 1220 may be attached to the thumb wheel 122 as illustrated in FIGS. 5-6. The push/pull cable 1220 may be disposed within a central lumen 1230 in the shaft 110 of the catheter from the proximal end of the shaft 110 to the tip assembly 1110, wherein it then passes through an outer lumen 1240 of the tip assembly 1110. The distal end of the push/pull cable 1220 emanates through a slit 1250 in the tip assembly 1110. It should be appreciated that in embodiments where it is desired that the push/pull cable 1220 not be electrically connected to the electrode, the push/pull cable 1220 may be attached to the plastic slider 1210, rather than to the electrode 146a. It should also be appreciated that the push/pull wire 1220 need not be made from metal, as non-conducting materials may also be used, as known to those skilled in the art.

FIG. 13 is a cross sectional erid view of distal end of the tip assembly 1110 illustrated in FIG. 12, taken along line 13-13. FIG. 13 illustrates the slit 1250 in the distal end of the tip assembly 1110 through which the push/pull cable 1220 protrudes. The tip assembly 1110 may include a number of other lumens 1310 that may be used to hold other cables to provide steering of the tip assembly, etc. Further details of the sliding electrode described with respect to FIGS. 11-13 are provided in commonly assigned U.S. Pat. No. 6,245,066, which is incorporated herein by reference in its entirety.

Figure 14:
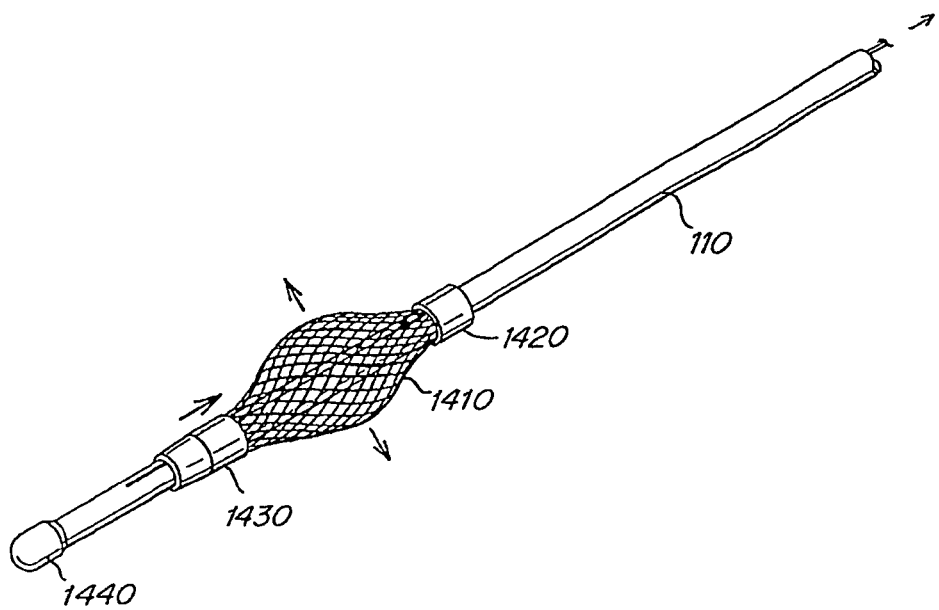
FIG. 14 is a perspective view of a distal end of the catheter that includes a braided conductive mesh that may be radially expanded and collapsed about the circumference of the shaft of the catheter.
Figure 15:
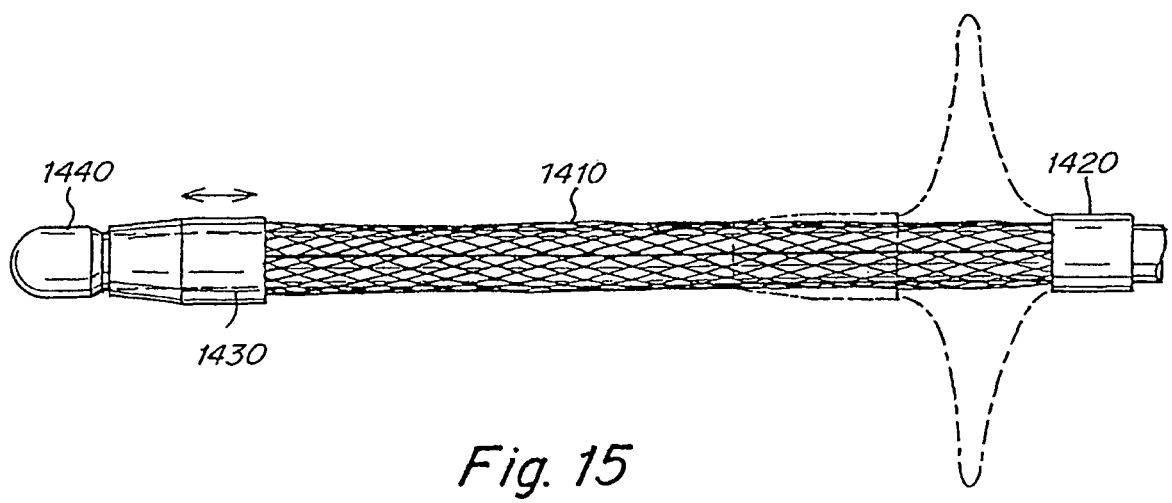
FIG. 15 is a side view of the distal end of the catheter illustrated in FIG. 14, showing the braided conductive mesh in a collapsed state.

FIGS. 14 and 15 illustrate a catheter in which the distal end of the catheter shaft 110 includes a braided conductive mesh 1410 that may be expanded (deployed) and collapsed (un-deployed) radially about the distal end of the catheter. As illustrated, the distal end of the catheter includes a first collar 1420 that is used to secure a proximal end of the conductive mesh 1410 in a fixed position around the circumference of the shaft 110, and a second and movable collar 1430 that is used to secure the distal end of the conductive mesh 1410 around the circumference of the shaft 110. The second collar 1430 may be moved proximally and distally along the distal end of the shaft 110 through the use of a cable, for example cable 230 (FIGS. 2-4) attached to an actuator 122, 124 on the handle 120. For example, where the distal end of the cable 230 is attached to the second collar 1430 and the proximal end of the cable 230 is attached to the slide actuator 124, movement of the slide actuator 124 in a proximal direction causes the second collar to move proximally along the shaft and causes the braided conductive mesh 140 to expand in a radial direction, as illustrated in FIG. 14, and in phantom in FIG. 15. Movement of the slide actuator 124 in a distal direction results in collapsing of the braided conductive mesh 1410. It should be appreciated that the operation of the first and second collars may be reversed, such that the first collar 1420 is movable and the second collar 1430 is fixed in position. The distal tip portion of the catheter shaft 110 may include a cap 1440, which may be made from an electrically insulating material, or an electrically conductive material, such that the cap 1440 may be used as an electrode.

Figure 16:
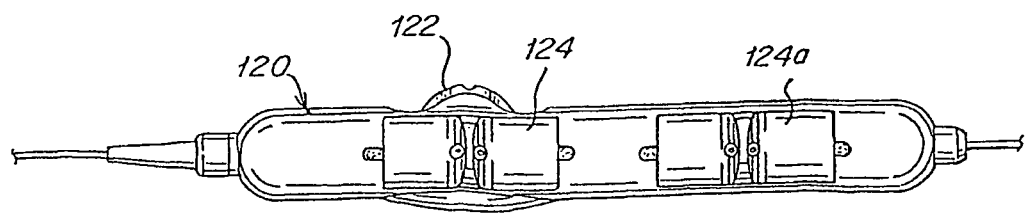
FIG. 16 is an elevational view of another handle that may be used with the catheter system of FIG. 1 according to another embodiment of the invention that includes a third actuator.

FIG. 16 illustrates another handle that may be used with embodiments of the present invention. In the embodiment depicted in FIG. 16, the handle 120 includes three actuators 122, 124, and 124a. For example, the handle may include a thumb wheel actuator 122, and two slide actuators 124, 124a. One or more of these actuators may be used to operate a cable attached thereto in both tension and compression, for controlling operation of the catheter. For example, the thumb wheel actuator 122 may be used to change the orientation of the distal end of the catheter relative to the longitudinal axis of the shaft 110 in one or two different directions. The first slide actuator 124 may be used to increase and/or decrease the radius of curvature of an arcuately curved distal end of a tip assembly attached to the distal end of the catheter, and the second slide actuator 124a may be used to control the orientation of the of the tip assembly relative to the longitudinal axis of the shaft 110 of the catheter 100 in one or two different direction of movement that are orthogonal to the directions provided by use of the thumb wheel actuator 122. Alternatively, the second slide actuator 124A may be used to move a sliding electrode proximally and distally along the distal end of the tip assembly. Alternatively still, the thumbwheel actuator 122 or the first slide actuator 124 may be used for changing the orientation of the tip assembly or the radius of curvature of the distal end in a first direction, and the second slide actuator 124a may be used for changing the orientation of the tip assembly or the radius of curvature in the opposite direction. Alternatively still, the first slide actuator 124 may be used for controlling an active bend (see FIG. 21), the thumbwheel actuator 122 may be used for changing the radius of curvature of the distal end of the tip assembly, and the second slide actuator 124a may be used for changing the orientation of the tip assembly in a first and/or second direction (e.g., for steering of the proximal end of the tip assembly.)

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A catheter comprising:
   a handle comprising:
      a housing having a proximal end, a distal end, and a longitudinal axis that extends from the proximal end of the housing to the distal end of the housing;
      a cable, disposed in the housing, that extends through the proximal end of the housing, a portion of the cable that is disposed in the housing being movable, under compression, in a first direction that is substantially aligned with the longitudinal axis of the housing; and
      a guide, disposed in the housing, adapted to prevent the portion of the cable from moving in a second direction that is transverse to the first direction when the portion of the cable is moved in the first direction; and
   an elongated shaft, a proximal end of the elongated shaft being attached to the distal end of the housing, wherein the cable extends through the distal end of the housing and into the elongated shaft;
   wherein a distal end of the elongated shaft is coupled to a conductive braided mesh; and
   wherein a distal end of the cable is coupled to a distal end of the braided mesh, and wherein the distal end of the braided mesh is movable distally in response to movement of the portion of the cable in the first direction.

2. The catheter of claim 1, wherein the guide includes:
   a hollow mandrel formed from a material that is stiffer, in compression, than the cable, the cable being disposed within the mandrel; and
   a retainer, attached to the housing and the mandrel, to retain the mandrel in a fixed position within the housing.

3. The catheter of claim 2, wherein the mandrel is cylindrically shaped.

4. The catheter of claim 2, wherein the mandrel has a length that is approximately twenty percent of a length of the portion of the cable.

5. The catheter of claim 1, wherein the guide is separate from the housing and removably attached thereto.

6. The catheter of claim 1, wherein the cable is approximately 0.011 inches in diameter.

7. The catheter of claim 1, wherein the catheter is an electrophysiology catheter.

8. The catheter of claim 1, wherein the portion of the cable that is disposed in the housing is movable, under compression, proximally relative to the housing in the first direction.

9. The catheter of claim 1, wherein the portion of the cable that is disposed in the housing is movable, under compression, distally relative to the housing in the first direction.

10. The catheter of claim 9, wherein the portion of the cable that is disposed in the housing is movable, under tension, proximally relative to the housing in a third direction that is opposite the first direction.

11. The catheter of claim 1, wherein the elongated shaft has a diameter of approximately 6 French.

12. The catheter of claim 1, wherein a distal end of the cable is attached to a distal end of the elongated shaft, and wherein the distal end of the elongated shaft is movable relative to a proximal end of the elongated shaft in response to movement of the portion of the cable in the first direction.

13. The catheter of claim 1, wherein the catheter for use with the handle comprises an elongate shaft, and wherein the guide is separate from the elongated shaft.

14. The catheter of claim 1, wherein the guide includes a mandrel having a through-hole occupied by a portion of the cable, wherein the through-hole is sized and shaped to prevent the portion of the cable occupying the through-hole from moving in any direction transverse to the first direction.

15. The catheter of claim 14, wherein the through-hole has a diameter that is 25 to 50 percent greater than an outer diameter of the cable.

16. The handle catheter of claim 14, wherein the through-hole has a diameter that is 10 to 20 percent greater than an outer diameter of the cable.

17. A catheter comprising:
a handle comprising:
  a housing having a proximal end, a distal end, and a longitudinal axis that extends from the proximal end of the housing to the distal end of the housing;
  a cable, disposed in the housing, that extends through the proximal end of the housing, a portion of the cable that is disposed in the housing being movable, under compression, in a first direction that is substantially aligned with the longitudinal axis of the housing; and
  a guide, disposed in the housing, adapted to prevent the portion of the cable from moving in a second direction that is transverse to the first direction when the portion of the cable is moved in the first direction; and
an elongated shaft, a proximal end of the elongated shaft being attached to the distal end of the housing, wherein the cable extends through the distal end of the housing and into the elongated shaft;
wherein a distal end of the elongated shaft includes at least one electrode; and
wherein a distal end of the cable is attached to the at least one electrode, and wherein the at least one electrode is movable distally along the distal end of the elongated shaft in response to movement of the portion of the cable in the first direction.

18. The catheter of claim 17, wherein a distal end of the elongated shaft includes a tip assembly has an arcuate curve, wherein a distal end of the cable is attached to a distal end of the tip assembly, and wherein a radius of curvature of the arcuate curve is adjustable in response to movement of the portion of the cable in the first direction.

19. A catheter comprising:
a handle comprising:
  a housing having a proximal end, a distal end, and a longitudinal axis that extends from the proximal end of the housing to the distal end of the housing;
  a cable, disposed in the housing, that extends through the proximal end of the housing, a portion of the cable that is disposed in the housing being movable, under compression, in a first direction that is substantially aligned with the longitudinal axis of the housing; and
  a guide, disposed in the housing, adapted to prevent the portion of the cable from moving in a second direction that is transverse to the first direction when the portion of the cable is moved in the first direction; and
an elongated shaft, a proximal end of the elongated shaft being attached to the distal end of the housing, wherein the cable extends through the distal end of the housing and into the elongated shaft;
wherein a distal end of the elongated shaft is coupled to a conductive braided mesh; and
wherein a distal end of the cable is attached to a proximal end of the braided mesh, and wherein the proximal end of the braided mesh is movable distally along the distal end of the elongated shaft in response to movement of the portion of the cable in the first direction.

20. A catheter comprising:
a handle comprising:
  a housing having a proximal end, a distal end, and a longitudinal axis that extends from the proximal end of the housing to the distal end of the housing;
  a cable, disposed in the housing, that extends through the proximal end of the housing, a portion of the cable that is disposed in the housing being movable, under compression, in a first direction that is substantially aligned with the longitudinal axis of the housing; and
  means for preventing the portion of the cable from moving in a second direction that is transverse to the first direction when the portion of the cable is moved in the first direction;
  wherein the portion of the cable that is disposed in the housing is movable, under compression, distally relative to the housing in the first direction; and
an elongated shaft, a proximal end of the elongated shaft being attached to the distal end of the housing, wherein the cable extends through the distal end of the housing and into the elongated shaft;
wherein a distal end of the elongated shaft is coupled to a conductive braided mesh, wherein a distal end of the cable is attached to one of a distal end and a proximal end of the braided mesh, and wherein the one of the distal end and the proximal end of the braided mesh is movable distally in response to movement of the portion of the cable in the first direction.

21. The catheter of claim 20, wherein the means for preventing includes:
  a hollow mandrel formed from a material that is stiffer, in compression, than the cable, the cable being disposed within the mandrel; and
  means for retaining the mandrel in a fixed position within the housing.

22. The catheter of claim 21, wherein the mandrel is cylindrically shaped.

23. The catheter of claim 21, wherein the mandrel has a length that is approximately twenty percent of a length of the portion of the cable.

24. The catheter of claim 20, wherein the means for preventing is removably attached within the housing.

25. The catheter of claim 20, wherein the catheter is an electrophysiology catheter.

26. The catheter of claim 20, wherein the portion of the cable that is disposed in the housing is movable, under compression, distally relative to the housing in the first direction.

27. The catheter of claim 26, wherein the portion of the cable that is disposed in the housing is movable, under tension, proximally relative to the housing in a third direction that is opposite the first direction.

28. The catheter of claim 26, wherein the catheter further comprises an elongated shaft, a proximal end of the elongated shaft being attached to the distal end of the housing, and wherein the cable extends through the distal end of the housing and into the elongated shaft.

29. The catheter of claim 28, wherein the elongated shaft has a diameter of approximately 6 French, and wherein the cable is approximately 0.011 inches in diameter.

30. The catheter of claim 20, wherein a distal end of the cable is attached to a distal end of the elongated shaft, and wherein the distal end of the elongated shaft is movable relative to a proximal end of the elongated shaft in response to movement of the portion of the cable in the first direction.

31. The catheter of claim 20, wherein the handle further comprises:
actuator means, attached to the housing, for applying a compressive force to the portion of the cable to move the portion of the cable in the first direction in response to movement of the actuator means.

32. The catheter of claim 20, wherein the means for preventing is separate from the elongated shaft.

33. A catheter comprising:
a handle comprising:
a housing having a proximal end, a distal end, and a longitudinal axis that extends from the proximal end of the housing to the distal end of the housing;
a cable, disposed in the housing, that extends through the proximal end of the housing, a portion of the cable that is disposed in the housing being movable, under compression, in a first direction that is substantially aligned with the longitudinal axis of the housing; and
means for preventing the portion of the cable from moving in a second direction that is transverse to the first direction when the portion of the cable is moved in the first direction;
wherein the portion of the cable that is disposed in the housing is movable, under compression, distally relative to the housing in the first direction; and
an elongated shaft, a proximal end of the elongated shaft being attached to the distal end of the housing, wherein the cable extends through the distal end of the housing and into the elongated shaft;
wherein a distal end of the elongated shaft includes at least one electrode, wherein a distal end of the cable is attached to the at least one electrode, and wherein the at least one electrode is movable distally along the distal end of the elongated shaft in response to movement of the portion of the cable in the first direction.

34. The catheter of claim 33, wherein a distal end of the elongated shaft includes a tip assembly has an arcuate curve, wherein a distal end of the cable is attached to a distal end of the tip assembly, and wherein a radius of curvature of the arcuate curve is adjustable in response to movement of the portion of the cable in the first direction.

35. A method of using a catheter having a handle, the handle having walls defining a cavity, a proximal end, a distal end, and a longitudinal axis that extends from the proximal end of the handle to the distal end of the handle, the method comprising acts of:
applying a compressive force to a portion of a cable that is disposed in the cavity to move the portion of the cable in a first direction that is substantially aligned with the longitudinal axis of the handle; and
within the cavity, constraining the portion of the cable such that the portion of the cable is prevented from moving in a second direction that is transverse to the first direction in response to the act of applying;
wherein the catheter includes an elongated shaft having a proximal end that is attached to the distal end of the handle, wherein the cable extends through the distal end of the handle and into the elongated shaft, wherein a distal end of the elongated shaft is coupled to a conductive braided mesh, and wherein a distal end of the cable is attached to one of a distal end and a proximal end of the braided mesh, the method further comprising an act of moving the one of the distal end and the proximal end of the braided mesh distally in response to movement of the portion of the cable in the first direction.

36. The method of claim 35, further comprising an act of:
applying a rotational force to an actuator that is disposed on the handle and attached to the portion of the cable to apply the compressive force to the portion of the cable.

37. The method of claim 35, further comprising an act of:
applying a linear force to an actuator that is disposed on the handle and attached to the portion of the cable to apply the compressive force to the portion of the cable.

38. The method of claim 35, wherein the catheter includes an elongated shaft having a proximal end that is attached to the distal end of the handle, wherein the cable extends through the distal end of the handle and into the elongated shaft, and wherein a distal end of the cable is attached to a distal end of the elongated shaft, the method further comprising an act of moving the distal end of the elongated shaft relative to the proximal end of the elongated shaft in response to movement of the portion of the cable in the first direction.

39. The method of claim 35, wherein the act of constraining comprises constraining the portion of the cable with a mandrel having a through-hole occupied by a portion of the cable, wherein the through-hole is sized and shaped to prevent the portion of the cable occupying the through-hole from moving in any direction transverse to the first direction.

40. The method of claim 39, wherein the through-hole has a diameter that is 25 to 50 percent greater than an outer diameter of the cable.

41. The method of claim 39, wherein the through-hole has a diameter that is 10 to 20 percent greater than an outer diameter of the cable.

42. A method of using a catheter having a handle, the handle having walls defining a cavity, a proximal end, a distal end, and a longitudinal axis that extends from the proximal end of the handle to the distal end of the handle, the method comprising acts of:
applying a compressive force to a portion of a cable that is disposed in the cavity to move the portion of the cable in a first direction that is substantially aligned with the longitudinal axis of the handle; and
within the cavity, constraining the portion of the cable such that the portion of the cable is prevented from moving in a second direction that is transverse to the first direction in response to the act of applying;
wherein the catheter includes an elongated shaft having a proximal end that is attached to the distal end of the handle, wherein the cable extends through the distal end of the handle and into the elongated shaft, and wherein a distal end of the elongated shaft includes at least one electrode that is movably attached to a distal end of the cable, the method further comprising an act of moving the at least one electrode distally along the distal end of the elongated shaft in response to movement of the portion of the cable in the first direction.

43. The method of claim 42, wherein the catheter includes an elongated shaft having a proximal end that is attached to the distal end of the handle, wherein the cable extends through the distal end of the handle and into the elongated shaft, wherein a distal end of the elongated shaft includes a tip assembly having an arcuate curve, and wherein a distal end of the cable is attached to a distal end of the tip assembly, the method further comprising an act of adjusting a radius of curvature of the arcuate curve in response to movement of the portion of the cable in the first direction.

44. A catheter comprising:
an elongated shaft; and
a handle comprising:
- a housing having a proximal end and a distal end, the distal end of the housing being attached to a proximal end of the elongated shaft;
- a cable, disposed in the housing, that extends through the distal end of the housing and into the elongated shaft;
- an actuator, attached to the housing and the cable, the actuator being movable between a first position in which the cable extends a first distance into the elongated shaft and a second position in which the cable extends a second distance into the elongated shaft, the second distance being less than the first distance; and
- a guide, disposed in the housing and separate from the elongated shaft, adapted to maintain a portion of the cable that is disposed between the distal end of the housing and the actuator when the actuator is in the second position in a substantially fixed lateral position when the actuator is moved toward the first position;
wherein a distal end of the elongated shaft is coupled to a conductive braided mesh; and
wherein a distal end of the cable is coupled to a distal end of the braided mesh, and wherein the distal end of the conductive braided mesh is movable proximally and distally in response to movement of the actuator.

45. The catheter of claim 44, wherein the guide includes:
a hollow mandrel formed from a material that is stiffer, in compression, than the cable, the cable being disposed within the mandrel; and
a retainer, attached to the housing and the mandrel, to retain the mandrel in a fixed position within the housing.

46. The catheter of claim 45, wherein the mandrel is cylindrically shaped.

47. The catheter of claim 45, wherein the mandrel has a length that is approximately twenty percent of a length of the portion of the cable that is disposed between the distal end of the elongated shaft and the actuator when the actuator is in the second position.

48. The catheter of claim 46, wherein the housing has a longitudinal axis that is aligned with the proximal end of the elongated shaft, and wherein the actuator is a slide actuator that is movable along the longitudinal axis of the housing.

49. The catheter of claim 48, wherein the substantially fixed lateral position is aligned with the longitudinal axis of the housing.

50. The catheter of claim 44, wherein the guide is separate from the housing and removably attached thereto.

51. The catheter of claim 44, wherein the guide is further adapted to maintain the portion of the cable that is disposed between the distal end of the housing and the actuator when the actuator is in the second position in the substantially fixed lateral position when the actuator is moved toward the second position.

52. The catheter of claim 44, wherein the actuator is a thumb wheel actuator.

53. The catheter of claim 44, wherein the cable is movable distally with respect to the housing in compression, and proximally with respect to the housing in tension.

54. The catheter of claim 44, wherein the cable is approximately 0.011 inches in diameter.

55. The catheter of claim 44, wherein the elongated shaft has a diameter of approximately 6 French.

56. The catheter of claim 44, wherein the catheter is an electrophysiology catheter.

57. The catheter of claim 44, wherein a distal end of the cable is attached to a distal end of the elongated shaft, and wherein the distal end of the elongated shaft is movable relative to a proximal end of the elongated shaft in response to movement of the actuator.

58. The catheter of claim 44, wherein the guide includes a mandrel having a through-hole occupied by a portion of the cable, and wherein the through-hole has a diameter that is 25 to 50 percent greater than an outer diameter of the cable.

59. The catheter of claim 44, wherein the guide includes a mandrel having a through-hole occupied by a portion of the cable, and wherein the through-hole has a diameter that is 10 to 20 percent greater than an outer diameter of the cable.

60. A handle for use with a catheter having an elongated shaft, the handle comprising:
a housing having a proximal end and a distal end, the distal end of the housing being attached to a proximal end of the elongated shaft;
a cable, disposed in the housing, that extends through the distal end of the housing and into the elongated shaft;
an actuator, attached to the housing and the cable, the actuator being movable between a first position in which the cable extends a first distance into the elongated shaft and a second position in which the cable extends a second distance into the elongated shaft, the second distance being less than the first distance; and
a guide, disposed in the housing and separate from the elongated shaft, adapted to maintain a portion of the cable that is disposed between the distal end of the housing and the actuator when the actuator is in the second position in a substantially fixed lateral position when the actuator is moved toward the first position;
wherein the actuator is a thumb wheel actuator; and
wherein the thumb wheel includes an arcuate wall, disposed on a proximal portion of the thumb wheel actuator, that prevents the cable from bowing in a lateral direction as the thumb wheel is rotated toward the first position.

61. The handle of claim 60, wherein the arcuate wall spans less than one hundred and eighty degrees.

62. A catheter comprising:
an elongated shaft; and
a handle, the handle comprising:
a housing having a proximal end and a distal end, the distal end of the housing being attached to a proximal end of the elongated shaft;
a cable, disposed in the housing, that extends through the distal end of the housing and into the elongated shaft;
an actuator, attached to the housing and the cable, the actuator being movable between a first position in which the cable extends a first distance into the elongated shaft and a second position in which the cable extends a second distance into the elongated shaft, the second distance being less than the first distance; and a guide, disposed in the housing and separate from the elongated shaft, adapted to maintain a portion of the cable that is disposed between the distal end of the housing and the actuator when the actuator is in the second position in a substantially fixed lateral position when the actuator is moved toward the first position;

wherein a distal end of the elongated shaft includes at least one electrode; and wherein a distal end of the cable is attached to the at least one electrode, and wherein the at least one electrode is movable proximally and distally along the distal end of the elongated shaft in response to movement of the actuator.

63. The catheter of claim 62, wherein a distal end of the elongated shaft includes a tip assembly has an arcuate curve, wherein a distal end of the cable is attached to a distal end of the tip assembly, and wherein a radius of curvature of the arcuate curve is adjustable in response to movement of the actuator.

64. A handle for use with a catheter having an elongated shaft, the handle comprising:

a housing having a proximal end and a distal end, the distal end of the housing being attached to a proximal end of the elongated shaft;

a cable, disposed in the housing, that extends through the distal end of the housing and into the elongated shaft;

an actuator, attached to the housing and the cable, the actuator being movable between a first position in which the cable extends a first distance into the elongated shaft and a second position in which the cable extends a second distance into the elongated shaft, the second distance being less than the first distance; and a guide, disposed in the housing and separate from the elongated shaft, adapted to maintain a portion of the cable that is disposed between the distal end of the housing and the actuator when the actuator is in the second position in a substantially fixed lateral position when the actuator is moved toward the first position;

wherein the cable is a first cable, the actuator is a first actuator, the guide is a first guide, and wherein the substantially fixed lateral position is a first substantially fixed lateral position, the handle further comprising:

a second cable, disposed in the housing, that extends through the distal end of the housing and into the elongated shaft;

a second actuator, attached to the housing and the second cable, the second actuator being movable between a third position in which the second cable extends a third distance into the elongated shaft and a fourth position in which the second cable extends a fourth distance into the elongated shaft, the fourth distance being less than the second distance; and a second guide, disposed in the housing, adapted to maintain a portion of the second cable that is disposed between the distal end of the housing and the second actuator when the second actuator is in the fourth position in a second substantially fixed lateral position when the second actuator is moved toward the third position.

65. The handle of claim 64, wherein the second cable is movable distally with respect to the housing in compression, and proximally with respect to the housing in tension.

* * * * *

UNITED STATES PATENT AND TRADEMARK OFFICE
CERTIFICATE OF CORRECTION

| | | |
|---|---|---|
| PATENT NO. | : 7,331,958 B2 | Page 1 of 1 |
| APPLICATION NO. | : 10/475941 | |
| DATED | : February 19, 2008 | |
| INVENTOR(S) | : Gary S. Falwell et al. | |

It is certified that error appears in the above-identified patent and that said Letters Patent is hereby corrected as shown below:

In Claim 16, line 12, "The handle catheter" should read -- The catheter --.

In Claim 48, line 51, "The catheter of claim 46" should read -- The catheter of claim 45 --.

Signed and Sealed this

Twenty-seventh Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,331,958 B2  Page 1 of 1
APPLICATION NO. : 10/475941
DATED : February 19, 2008
INVENTOR(S) : Gary S. Falwell et al.

It is certified that error appears in the above-identified patent and that said Letters Patent is hereby corrected as shown below:

Column 17, Claim 16, line 12, "The handle catheter" should read -- The catheter --.

Column 21, Claim 48, line 51, "The catheter of claim 46" should read -- The catheter of claim 45 --.

This certificate supersedes the Certificate of Correction issued May 27, 2008.

Signed and Sealed this

Twenty-fourth Day of June, 2008

JON W. DUDAS
*Director of the United States Patent and Trademark Office*